United States Patent
Piechnik et al.

(10) Patent No.: US 10,228,432 B2
(45) Date of Patent: Mar. 12, 2019

(54) SYSTEMS AND METHODS FOR GATED MAPPING OF T1 VALUES IN ABDOMINAL VISCERAL ORGANS

(71) Applicant: Oxford University Innovation Limited, Oxford (GB)

(72) Inventors: Stefan Piechnik, Oxford (GB); Rajarshi Banerjee, Oxford (GB); Elizabeth Tunnicliffe, Oxford (GB); Matthew Robson, Oxford (GB); Stefan Neubauer, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 46 days.

(21) Appl. No.: 14/364,736

(22) PCT Filed: Dec. 13, 2012

(86) PCT No.: PCT/GB2012/053118
§ 371 (c)(1),
(2) Date: Jun. 12, 2014

(87) PCT Pub. No.: WO2013/088151
PCT Pub. Date: Jun. 20, 2013

(65) Prior Publication Data
US 2014/0350385 A1    Nov. 27, 2014

Related U.S. Application Data

(60) Provisional application No. 61/630,510, filed on Dec. 13, 2011.

(30) Foreign Application Priority Data

Dec. 13, 2011   (GB) .................................. 1121406.1

(51) Int. Cl.
*A61B 5/055* (2006.01)
*G01R 33/54* (2006.01)
(Continued)

(52) U.S. Cl.
CPC ............ *G01R 33/543* (2013.01); *A61B 5/055* (2013.01); *A61B 5/1128* (2013.01);
(Continued)

(58) Field of Classification Search
USPC ........................................................ 600/413
See application file for complete search history.

(56) References Cited

U.S. PATENT DOCUMENTS 5,218,532 A   6/1993   Mori
5,322,682 A   6/1994   Bartzokis
(Continued)

FOREIGN PATENT DOCUMENTS

DE   10 2009 011382    9/2010
GB         2498254    9/2010
(Continued)

OTHER PUBLICATIONS

Sahani et al (Imaging the liver).*
(Continued)

*Primary Examiner* — Joel F Brutus
(74) *Attorney, Agent, or Firm* — Thomas | Horstemeyer, LLP

(57) ABSTRACT

The present disclosure provides systems and methods for universal mapping of T1 in abdominal organs using cardiac gating. A region of interest is selected for mapping or imaging. A determination is made whether any one or more of heart associated motion, high heart rate and irregular heart beat are detected in the region of interest. A multi-pathway (Continued)

gating of T1 maps is then employed providing a universal method of T1 mapping of moving as well as non-moving visceral organs.

16 Claims, 9 Drawing Sheets

(51) Int. Cl.
    *A61B 5/00*           (2006.01)
    *A61B 5/11*           (2006.01)
    *G01R 33/50*         (2006.01)
    *A61B 5/0402*        (2006.01)
    *G01R 33/567*        (2006.01)

(52) U.S. Cl.
    CPC ............ *A61B 5/7285* (2013.01); *G01R 33/50* (2013.01); *G01R 33/5673* (2013.01); *A61B 5/04021* (2013.01); *G01R 33/5676* (2013.01)

(56) References Cited

U.S. PATENT DOCUMENTS

| | | | |
|---|---|---|---|
| 5,908,386 A * | 6/1999 | Ugurbil | G01R 33/56341 |
| | | | 324/306 |
| 5,993,398 A | 11/1999 | Alperin | |
| 6,245,027 B1 | 6/2001 | Alperin | |
| 6,605,943 B1 | 8/2003 | Clark et al. | |
| 2004/0102692 A1 | 5/2004 | Schenck | |
| 2004/0155653 A1 | 8/2004 | Larson | |
| 2005/0197586 A1 | 9/2005 | Pearlman | |
| 2007/0247153 A1 | 10/2007 | Yu et al. | |
| 2008/0012563 A1* | 1/2008 | Weiss | G01R 33/4824 |
| | | | 324/307 |
| 2008/0150532 A1 | 6/2008 | Slavin | |
| 2010/0198050 A1 | 8/2010 | Mori | |
| 2010/0241012 A1 | 9/2010 | Yin et al. | |
| 2011/0028828 A1 | 2/2011 | Daye et al. | |
| 2011/0181285 A1 | 7/2011 | Greiser | |

FOREIGN PATENT DOCUMENTS

| | | |
|---|---|---|
| WO | 20060134430 | 12/2006 |
| WO | 20130046158 | 4/2013 |
| WO | 20130088149 | 6/2013 |
| WO | 20130088151 | 6/2013 |
| WO | 20140011925 | 1/2014 |
| WO | 20140140635 | 9/2014 |
| WO | 20150155521 | 10/2015 |

OTHER PUBLICATIONS

International Search Report Application No. PCT/GB2012/053118 dated Mar. 6, 2013, 12 pages.
GB Search Report Application No. GB1121406.1 dated Mar. 13, 2012, 3 pages.
Standish RA et al Gut. Apr. 2006;55(4):569-78. An appraisal of the histopathological assessment of liver fibrosis.
Thomsen, et al. Prolonged T1 in patients with liver cirrhosis: An in vivo MRI study. Magn Reson Imaging. 1990; 8:599-604.
Varghese T et al. "Elastographic imaging using a handheld compressor." Ultrason Imaging. Jan. 2002;24(1):25-35.
Versluis et al., Detection of cerebral microbleeds: Physical principles, technical aspects and new developments. In: Cerebral Microbleeds ed. Werring DJ. Cambridge University Press, 2011; pp. 13-21.
Vymazal et al., 1992 T1 and T2 of ferritin at different field strengths: Effect on MRI. Magn Reson Med. 1992; 27:367-74.
Vymazal et al. 1996 The relation between brain iron and NMR relaxation times: An in vitro study. Magn Reson Med. 1996; 35:56-61.

Wood, et al. MRI R2 and R2* mapping accurately estimates hepatic iron concentration in transfusion-dependent thalassemia and sickle cell disease patients. Blood. 2005; 106:1460-5).
Clinical NMR Group. "Magnetic resonance imaging of parenchymal liver disease: a comparison with ultrasound, radionuclide scintigraphy and X-ray computed tomography." Clinical Radiology 38.5 (1987): 495-502.
van Werven et al. Assessment of Hepatic Steatosis in Patients Undergoing Liver Resection: Comparison of US, CT, T1-weighted Dual-Echo MR Imaging,and Point-resolved 1 H MR Spectroscopy, Radiology: vol. 256: No. 1—Jul. 2010.
McPherson et al. Magnetic resonance imaging and spectroscopy accurately estimate the severity of steatosis provided the stage of fibrosis is considered. Journal of Hepatology, vol. 51, Issue 2, Aug. 2009, pp. 389-397.
RM SSE, http://www.uta.edu/faculty/sawasthi/Statistics/glosr.html Nov. 2007.
Aisen, et al. Detection of liver fibrosis with magnetic cross-relaxation. Magn Reson Med. 1994; 31:551-6).
Alanen et al., Acta. Radiol., Jul. 1998; 39 (4): 434-9. "MR and magnetisation transfer imaging in cirrhotic and fatty livers."
Bacic et al. NMR study of water exchange across the hepatocyte membrane. Magn Reson Imaging 1989; 7:411-416.
Banerjee et al "Multiparametric Magnetic Resonance for the non-invasive diagnosis of liver disease." J Hepatol. (2014) 60(1):69-77.
Bohte, A. E., A. de Niet, et al. "Non-invasive evaluation of liver fibrosis: a comparison of ultrasound-based transient alastography and MR elastography in patients with viral hepatitis B and C." Eur Radiol 24(3): 638-48. Oct. 2013.
Bosch, J., J. G. Abraldes, et al. (2009). "The clinical use of HVPG measurements in chronic liver disease." Nat Rev Gastroenterol Hepatol 6(10): 573-582.
Bravo, A. A.,et al. (2001). "Liver Biopsy." New England Journal of Medicine 344(7): 495-500.
Bredella MA, et al J Comput Assist Tomogr. May-Jun. 2010;34(3):372-6. Breath-hold 1H-magnetic resonance spectroscopy for intrahepatic lipid quantification at 3 Tesla.
British Liver Trust, 2006 Alcohol and liver disease. Ringwood: British Liver Trust, 2006.
Chamuleau, et al. Is the magnetic resonance imaging proton spin-lattice relaxation time a reliable noninvasive parameter of developing liver fibrosis? Hepatology. 1988; 8:217-21.
Cheng J. Magnetic Resonance Imaging (2012) 36(4): 805-824.
Colecchia A, et al Measurement of spleen stiffness to evaluate portal hypertension and the presence of esophageal varices in patients with HCV-related cirrhosis. Gastroenterology. Sep. 2012;143(3):646-54.
Ekstedt M, et al. Hepatology 2006; 44: 865. Long-term follow-up of patients with NAFLD and elevated liver enzymes.
El Badry AM et al, Annals of Surgery 250(5), Nov. 2009, 691-697. Assessment of Hepatic Steatosis by Expert Pathologists: The End of a Gold Standard.
Ferreira VM, et al Non-contrast T1-mapping detects acute myocardial edema with high diagnostic accuracy: a comparison to T2-weighted cardiovascular magnetic resonance .J Cardiovasc Magn Reson 2012;14:42.
Fleming, Kate M., et al. "Abnormal liver tests in people aged 75 and above: prevalence and association with mortality." Alimentary pharmacology & therapeutics 34.3 (2011): 324-334.
Ghugre and Wood Relaxivity-iron calibration in hepatic iron overload: probing underlying biophysical mechanisms using a Monte Carlo model. Magn Reson Med 2011; 65:837-847.
Ghugre et al. Multi-field behavior of Relaxivity in an Iron-rich environment. Proc Intl Soc Mag Reson Med. 2008; 16:644).
Ghugre et al., Mechanisms of tissue-iron relaxivity: nuclear magnetic resonance studies of human liver biopsy specimens. Magn Reson Med. 2005; 54:1185-93.
Goldberg, et al. Hepatic cirrhosis: magnetic resonance imaging. Radiology. 1984; 153:737-9.
Graham and Henkelman Understanding pulsed magnetisation transfer. J Magn Reson Imaging 1997; 7:903-912.
Guo H. et al., J Magn Reson Imaging, Aug. 2009; 30(2):394-400. Myocardial T2 Quantitation in Patients With Iron Overload at 3 Tesla.

(56) References Cited

OTHER PUBLICATIONS

Henninger, et al. Evaluation of MR imaging with T1 and T2* mapping for the determination of hepatic iron overload. Eur Radiol. 2012; 22:2478-86.

Heye, et al. MR relaxometry of the liver: significant elevation of T1 relaxation time in patients with liver cirrhosis. Eur Radiol. 2012; 22:1224-32.

Hilt PJ Thesis, Quantification of Cardiac Longitudinal Relaxation (T1) AT 3.0 T During Normal and Hyperoxic Breathing Conditions, Aug. 2008.

Hines CDG et al. Radiology; 254: 1; Jan. 2010 Quantification of Hepatic Steatosis with 3T MR Imaging: Validation in ob/ob Mice.

Ishak et al., Histological grading and staging of chronic hepatitis. J Hepatol. 1995; 22:696-9.

Janiec DJ et al, Obes Surg. Apr. 2005;15(4):497-501. Histologic variation of grade and stage of non-alcoholic fatty liver disease in liver biopsies.

Keevil, et al. Non-invasive assessment of diffuse liver disease by in vivo measurement of proton nuclear magnetic resonance relaxation times at 0.08 T. Br J Radiol. 1994; 67:1084-1087).

Kim, et al. Quantitative evaluation of liver cirrhosis using T1 relaxation time with 3 tesla MRI before and after oxygen inhalation. J Magn Reson Imaging. 2012; 36:405-10.

Klasen J, et al Diffusion-weighted imaging (DWI) of the spleen in patients with liver cirrhosis and portal hypertension. Magn Reson Imaging. Sep. 2013;31(7):1092-6.

Li Zhou et al PLOS One (2013) 8(12): e83697.

Mackay A et al Magnetic Resonance in Medicine (1994) 32(6): 673-677.

Merkel, C. and S. Montagnese "Hepatic venous pressure gradient measurement in clinical hepatology." Digestive and Liver Disease 43(10): 762-767.

Messroghli DR et al, 2007 Optimization and Validation of a Fully-Integrated Pulse Sequence for Modified Look-Locker Inversion-Recovery (MOLLI) T1 Mapping of the Heart, Journal of Magnetic Resonance Imaging 26:1081-1086, 2007.

Messroghli DR, et al, 2004 Magn Reson Med 2004; 52:141-146. Modified Look-Locker inversion recovery (MOLLI) for high-resolution T1 mapping of the heart.

Nedredal GI et al Portal hypertension correlates with splenic stiffness as measured with MR elastography. J Magn Reson Imaging. Jul. 2011;34(1):79-87.

Patch, D., et al. (1999). "Single portal pressure measurement predicts survival in cirrhotic patients with recent bleeding." Gut 44(2): 264-9.

Perello A, et al (1999). "Wedged hepatic venous pressure adequately reflects portal pressure in hepatitis C virus-related cirrhosis." Hepatology 30(6): 1393-1397.

Piechnik SK, et al, 2010 J Cardiovasc Magn Reson. Nov. 19, 2010;12:69. Shortened Modified Look-Locker Inversion recovery (ShMOLLI) for clinical myocardial T1-mapping at 1.5 and 3 T within a 9 heartbeat breathhold.

Piechnik SK et al, 2013 "Normal variation of magnetic resonance T1 relaxation times in the human population at 1.5 T using ShMOLLI." J Cardiovasc Magn Reson 15: 13.

Regev A et al, Am J Gastroenterol. Oct. 2002; 97(10):2614-8. Sampling error and intra-observer variation in liver biopsy in patients with chronic HCV infection.

Rincon D et al. (2007). "Prognostic value of hepatic venous pressure gradient for in-hospital mortality of patients with severe acute alcoholic hepatitis." Aliment Pharmacol Ther 25(7): 841-8.

Ripoll C et al. (2005). "Influence of hepatic venous pressure gradient on the prediction of survival of patients with cirrhosis in the MELD Era." Hepatology 42(4): 793-801.

Rohrer et al., Comparison of magnetic properties of MRI contrast media solutions at different magnetic field strengths. Invest Radiol. 2005; 40:715-24.

Siegelman E S, MR imaging of diffuse liver disease. Hepatic fat and iron pp. 347-365. Magnetic resonance imaging clinics of North America, vol. 5, May 1997, United States.

St Pierre, et al. Noninvasive measurement and imaging of liver iron concentrations using proton magnetic resonance. Blood. 2005; 105:855-61.

Koenig, Seymour H., and Rodney D. Brown. "Relaxometry of tissue." Encyclopedia of Magnetic Resonance, (2007): 1-13.

De Miguel M H et al,"Evaluation of quantitative magnetic resonance imaging as a noninvasive technique for measuring renal scarring in a rabbit model of antiglomerular basement membrane disease.", Journal of the American Society of Nephrology: JASN May 1994, (May 1994), vol. 4, No. 11, pp. 1861-1868.

Ling C R et al, "Changes in NMR relaxation time associated with local inflammatory response", Physics in Medicine and Biology, Institute of Physics Publishing, Bristol GB, (Jun. 1, 1982), vol. 27, No. 6, pp. 853-860.

Squires Jr. et al, "Acute Liver Failure in Children: The First 348 Patients in the Pediatric Acute Liver Failure Study Group", J Pediatr. May 2006;148(5):652-658.

* cited by examiner

SYSTEMS AND METHODS FOR GATED MAPPING OF T1 VALUES IN ABDOMINAL VISCERAL ORGANS

CROSS-REFERENCE TO RELATED APPLICATIONS

This application is the National Stage of International Application No. PCT/GB2012/053118, filed 13 Dec. 2012, which claims the benefit of and priority to GB application 1121406.1, filed 13 Dec. 2011 and U.S. provisional application 61/630,510, filed 13 Dec. 2011, having the title "SYSTEMS AND METHODS FOR GATED MAPPING OF T1 VALUES IN ABDOMINAL VISCERAL ORGANS", the contents of all of which are incorporated by reference as if fully set forth herein.

TECHNICAL FIELD

The present disclosure generally relates to medical imaging and, more particularly, relates to systems and methods for performing an optimized, universal method for mapping of T1 in abdominal organs.

BACKGROUND

In magnetic resonance (MR) imaging, tissue contrast is generated by a combination of intrinsic tissue properties such as spin-lattice (T1) and spin-spin (T2) relaxation times, and extrinsic properties such as imaging strategies and settings. Signal intensity in conventional MR images is displayed on an arbitrary scale, and thus is not adequate for direct comparisons.

A major advantage of T1-mapping is absolute quantification of structural changes that is largely independent of imaging parameters, allowing for objective comparisons between examinations. T1 relaxation times depend on the composition of tissues, and while not unique for any specific tissue type, they exhibit characteristic ranges of normal values at a selected magnetic field strength. Changes in tissue composition can either increase or decrease T1 values. For example, increased extracellular fluid is associated with increased T1. Deviation from established ranges can thus be used to quantify the effects of pathological processes. Focal and global T1 changes are reported in a number of parenchymal tissue diseases, such as infarction, fibrosis, steatosis, and systemic diseases such as diabetes mellitus, amyloidosis, sarcoidosis and systemic lupus erythematosus.

T1-mapping may be a sensitive technique for detecting, for example, diffuse fibrosis in heart failure and valvular heart disease. Image acquisition, however, is affected by motion due to aortic and cardiac pulsation and to respiratory movement, which can generate artefacts. Therefore cardiac-gated T1 maps acquired with minimal heart associated movement, in addition to minimal respiratory movement of the diaphragm are preferred for consistency.

One method for performing myocardial T1-mapping is the modified Look Locker inversion recovery (MOLLI) pulse sequence. The MOLLI pulse sequence merges images from three consecutive inversion-recovery (IR) experiments into one data set and has been used to generate single-slice T1 maps of the myocardium. It is generally described in Messroghli D R, Radjenovic A. Kozerke S, Higgins D M, Sivananthan M U, Ridgway J P. Modified Look-Locker inversion recovery (MOLLI) for high-resolution T1 mapping of the heart. Magn Reson Med 2004; 52:141-146 which is incorporated by reference as if fully set forth herein.

The MOLLI technique is triggered by heart beat and attempts to generate a T1 map during a single breath-hold while the heart is not moving. The MOLLI technique does not address high heart rate or irregular heart beat. Moreover, the MOLLI technique involves relatively long recovery epochs, prolonging measurement time. Thus, one perceived shortcoming with the MOLLI technique is the long 17 heart-beat breath-hold required to perform MOLLI. Such a long period may be challenging for many patients who suffer from breathlessness, especially older or obese subjects.

Additionally, currently there are no clinical quantitative magnetic resonance (MR) protocols for the diagnosis of disease in non-moving visceral organs, such as the liver or pancreas, which may be subject to heart associated movement or pulsation. Previously published studies have concluded, for example, that there is no justification for the use of proton nuclear magnetic resonance imaging techniques or the in vivo measurement of hepatic T1 relaxation time. ("MRI of parenchymal liver disease.", Clin. Radiol. 1987 September; 38 (5): 495-502; Aisen et al., "Detection of liver fibrosis with magnetic cross-relaxation.", Magn. Reson. Med. 1994 May; 31 (5): 551-6; Alanen et al., "MR and magnetisation transfer imaging in cirrhotic and fatty livers.", Acta. Radiol., 1998 July; 39 (4): 434-9). For a clinically useful tool, further refinement in MR imaging to assess parenchymal tissue fibrosis has been desired to allow differentiation between non-alcoholic fatty liver disease (NAFLD), which is relatively benign, and non-alcoholic steatohepatitis (NASH), which has a worse prognosis and is more strongly linked to coronary artery disease.

Accordingly, there is a need to address the aforementioned deficiencies and inadequacies.

SUMMARY

Various embodiments of universal systems and methods for mapping of visceral organs are described herein. The embodiments include systems and methods for multi-pathway gated mapping of T1 which generate rapid and high resolution T1 maps of visceral organs.

In an embodiment, T1 mapping is optimized to provide imaging of visceral organs, for example the heart, liver and/or pancreas, in the same position in conjunction with cardiac gating. The optimization includes detecting heart associated motion in the region of interest and providing a multi-pathway for gating of T1 maps, for example, either by heart rate or artificially, depending upon the detection of motion. Additionally, high heart rate and an irregular heart beat can be accommodated by the present systems and methods. The present systems and methods, thus, provide a universal method of T1 mapping of moving as well as non-moving visceral organs.

In an exemplary embodiment, a method is provided that comprises: positioning a subject, for example a patient, in association with a magnetic resonance (MR) scanner; selecting an abdominal region for T1 mapping: and detecting whether heart associated motion is present in the selected region. The heart motion can be, for example, due to aortic or cardiac pulsation. If no motion is detected, the system and/or method artificially triggers T1 mapping of the selected region. If heart motion is detected, the system and/or method determines whether high heart rate and/or an irregular heart beat is present. If neither high heart rate nor irregular heart beat are detected then T1 mapping is triggered by heart beat. If either high heart rate or an irregular heart beat is present, the system and/or method artificially triggers T1 mapping of the selected region. Suitable methods for artificially triggering T1 mapping include use of simulated ECG available from the MR scanner or from a suitable device to trigger the mapping.

Another embodiment is a system comprising a magnetic resonance (MR) scanner, at least one computing device and at least one application executable in the at least one computing device, the at least one application comprising logic by which the present system and/or method selects an abdominal region for T1 mapping for a subject of interest and detects whether heart associated motion is present in the selected region. The heart motion can be, for example, due to aortic or cardiac pulsation. If no motion is detected, the system and/or method artificially triggers T1 mapping of the selected region. If heart associated motion is detected, the system and/or method determines whether high heart rate and/or an irregular heart beat is present. If neither high heart rate nor irregular heart beat are detected then T1 mapping is triggered by heart beat. If either high heart rate or an irregular heart beat is present, the system and/or method artificially triggers T1 mapping of the selected region. Suitable methods for artificially triggering T1 mapping include use of simulated ECG available from the MR scanner or from a suitable external device to trigger the mapping.

In any one or more of the embodiments herein, shimming, frequency shifting and/or fat saturation can be performed as needed for image quality assessment for the selected visceral organ(s). This method can assure that a set of comparable T1 maps of the visceral organ(s) are acquired having the same metrological properties independently of whether cardiac or artificial triggering or gating is used.

In any of the embodiments herein, there are a number of ways by which T1 mapping can be acquired. For example, the T1 mapping can be acquired using the MR scanner by using repeated inversion recovery (IR) experiments. Examples of suitable inversion recovery experiments include an inversion recovery (IR) pulse sequence, such as MOLLI (with the deficiencies described earlier), or a shortened version of the MOLLI sequence (Sh-MOLLI) to generate T1 maps of visceral organs in a single, significantly shorter breath-hold than that of the MOLLI sequence.

In any one or more of the embodiments herein, in circumstances when a shortened breath-hold is desired, a shortened MOLLI (Sh-MOLLI) technique can be applied in which consecutive inversion-recovery (IR) experiments are performed that include front-loaded sampling followed by one or more subsequent samples and conditionally including the subsequent one or more samples for the T1 mapping of the visceral organ(s) based on empirical relationships between the estimated spin-lattice relaxation time T1, heart rate, heart beat period or experimentally achieved relaxation recovery times or degrees, and estimated fit error associated with the subsequent experiments and samples.

In an embodiment the Sh-MOLLI technique comprises performing consecutive inversion-recovery (IR) experiments, wherein the consecutive IR experiments comprise a first IR experiment, a second IR experiment, and a third IR experiment, the first IR experiment comprising a number of samples exceeding a number of samples of both the second IR experiment and the third IR experiment. The technique further comprises conditionally processing the samples in the first, second, and third IR experiments.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
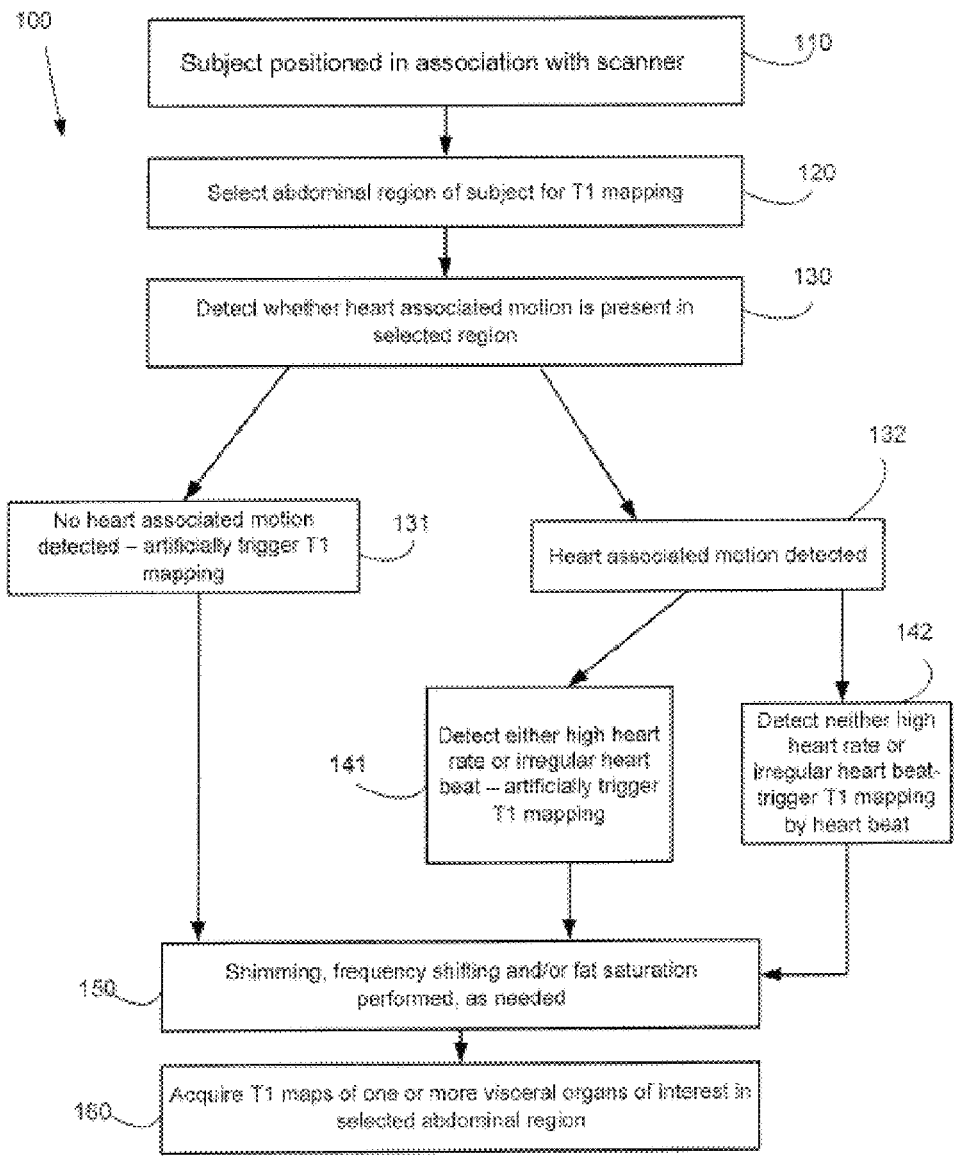
FIG. 1 is a flow chart illustrating one embodiment of a method of acquisition of an optimized T1 map of a visceral organ of the present disclosure.

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

Magnetic resonance (MR) can be used to measure tissue characteristics that can be used to determine the presence and severity of disease in visceral organs. T1-mapping may be a sensitive technique for detecting diffuse fibrosis in heart failure and valvular heart disease, which have been described by abnormal post-contrast T1 values but not by conventional late gadolinium enhanced (LGE) imaging.

We have discovered that high heart rate and/or irregular heart beat can adversely affect acquisition of myocardial T1 maps. We have also discovered T1-mapping may be a sensitive technique for detecting diffuse fibrosis in parenchymal liver and pancreatic diseases. For improved accuracy, however it is important to optimize the image acquisition and minimize heart associated motion due to, for example, aortic and cardiac pulsation, which can generate artefacts. Pulsation in large vessels in the visceral organs can cause error. Therefore cardiac-gated T1 maps acquired with minimal respiratory movement of the diaphragm are ideal for consistency.

To address these objectives we have developed the universal systems and methods for mapping of T1 of visceral organs, such as the heart, liver and pancreas, described herein. The present systems and methods provide a multipathway for gating of T1 maps of visceral organs, for example either by heart rate or artificially.

One embodiment of a system and method 100 of our present disclosure is illustrated in FIG. 1. In this embodiment, a subject, such as a patient, is positioned 110 in association with a magnetic resonance (MR) scanner and an abdominal region of the subject is selected 120 for T1 mapping. The system and/or method then detects 130 whether heart associated motion is present in the selected region. As an example, heart associated motion can be detected by acquiring a separate cine acquisition of the same imaging slice of the selected region using the MR scanner and looking for artifacts in the image slice. The motion can be, for example, due to aortic or cardiac pulsation. If no motion is detected, the system and/or method artificially triggers 131 T1 mapping of the selected region. If heart motion is detected 132, the system and/or method determines whether high heart rate and/or an irregular heart beat is present.

As an example, high heart rate might be determined as being present when the heart rate exceeds about 90 beats per minute (bpm) thresholds for high heart rate and irregular heart beat may be adjusted upwardly or downwardly based upon the patient. Further, as an example, an irregular heartbeat might be determined as being present when the R-R interval varies by more than about 20%. Though either or both high heart rate and irregular heart beat may vary from subject to subject.

If neither high heart rate nor irregular heart beat are detected then T1 mapping is triggered by heart beat 142. If either high heart rate or an irregular heart beat is present, the system and/or method artificially triggers 141 T1 mapping of the selected region. For example, a threshold of 95 beats may be used such that if the heart rate exceeds 95 beats per minute (bpm) then the system and/or method artificially triggers the T1 mapping. Other thresholds can be used. One suitable method for artificially triggering T1 mapping is the use of the simulated ECG available from the MR scanner or from a suitable external source to trigger the mapping.

Quantitative mapping of spin-lattice T1 relaxation times is then acquired using the MR scanner, for example, by use of repeated inversion recovery (IR) experiments. Shimming, frequency shifting and/or fat saturation can be performed 150 as needed for image quality assessment for the selected visceral organ(s). A set of comparable T1 maps of the visceral organ(s) are then acquired 160 having the same metrological properties independently of whether cardiac or artificial triggering or gating is used.

One suitable approach for providing quantitative mapping of spin-lattice (T1) relaxation time that uses repeated inversion recovery (IR) experiments is the modified Look Locker inversion (MOLLI) recovery pulse sequence. MOLLI merges images from three consecutive inversion-recovery (IR) experiments into one data set, generating single slice T1 maps of the liver. It is generally described in Messroghli D R, Radjenovic A. Kozerke S, Higgins D M, Sivananthan M U, Ridgway J P. Modified Look-Locker inversion recovery (MOLLI) for high-resolution T1 mapping of the heart. Magn Reson Med 2004; 52:141-146 which is incorporated by reference as if fully set forth herein.

The MOLLI sequence, however, can require relatively long recovery epochs, thereby prolonging the measurement time and progressively increasing the estimation errors for the long T1 relaxation times or fast heart rates. The relatively long recovery epochs required for the MOLLI technique can require a relatively long breath-hold. The breath-hold is required in order for the patient to remain still during the scan to avoid movement not only of the heart but also other visceral organs that we have discovered can incur artefacts associated to movement. For some patients the breath-hold required for the MOLLI technique is too long. Some patients are not capable of holding their breath for the required time.

Another approach for providing such experiments is a shortened version of the MOLLI sequence (referred to as Sh-MOLLI) described herein which generates rapid and high-resolution spin-lattice (T1) maps without the use of contrast agents in a single short breath-hold involving less heartbeats and a shorter breath-hold than required for a MOLLI sequence. The Sh-MOLLI sequence is preferred, for example when a shorter breath-hold is desired. For some implementations, the shortened modified Look Locker inversion recovery (Sh-MOLLI) technique is performed in twelve heartbeats or less. Various embodiments of the Sh-MOLLI technique are based on an abbreviated T1 sampling scheme combined with the use of processing logic to distinguish between long and short T1 relaxation times in order to conditionally utilize available T1 samples for non-linear T1 fitting. See, generally, Piechnik S K, Ferreira V M, Dall'Armellina E, Cochlin L E, Greiser A, Neubauer S, Robson M D., Shortened Modified Look-Locker Inversion recovery (ShMOLLI) for clinical myocardial T1-mapping at 1.5 and 3 T within a 9 heartbeat breathhold, J Cardiovasc Magn Reson. 2010 Nov. 19; 12:69, which is incorporated by reference as if fully set forth herein.

One advantage of Sh-MOLLI sequence or technique is an approximately two-fold increase in speed of acquisition and readily available insensitivity to cardiovascular motion sources. T1 mapping can be achieved using the Sh-MOLLI technique with artificial triggering and with other methods for stationary parts of the body. However, the Sh-MOLLI technique offers additional flexibility and redundancy to assure that measurements are comparable between views that do not contain moving tissues (and could be imaged otherwise) and those that are subject to cardiac motion and must be cardiac-gated.

The additional variation in T1 estimates is much less than the 25-50% expected from the reduced number of samples likely due to the fact that the Sh-MOLLI technique is less susceptible to movement artifacts accumulated within shorter breath-holds. Further underestimation of T1 values is only minor, especially when compared to the known bias of MOLLI, which is in the order of 5%. Results of simulations and phantom measurements showed that the bias in the Sh-MOLLI T1 estimates is relatively stable across a wide range of T1 values and independent of heart rate variation. As such, embodiments of the Sh-MOLLI technique provide a fast, clinically applicable solution, which generate robust, quantitative single breath-hold T1 maps of the human visceral organs with high resolution.

The accuracy of T1 mapping is potentially dependent on T1 respiratory motion, heart rate (HR) and distortion from pulsatile vascular motion. Moreover, accurate visualization of the pancreas requires the acquisition of fat-saturated readouts to minimize the impact of surrounding adipose tissue on T1 identification.

It should be emphasized that Sh-MOLLI calculations are not dependent on heart rate (HR) but accuracy changes with underlying true T1s. For T1s longer than approximately 800 ms, the Sh-MOLLI error of underestimation is constant at 4%. This allows for easy correction of measured T1 errors in this range:

$$T1_{True} = \frac{T1_{Measured}}{1 + relativeError} \approx 1.04 \cdot T1_{Measured}$$

For shorter T1 values (<800 ms), this formula does not apply and estimation errors change from negative to positive for the very short T1s.

Figure 2A:
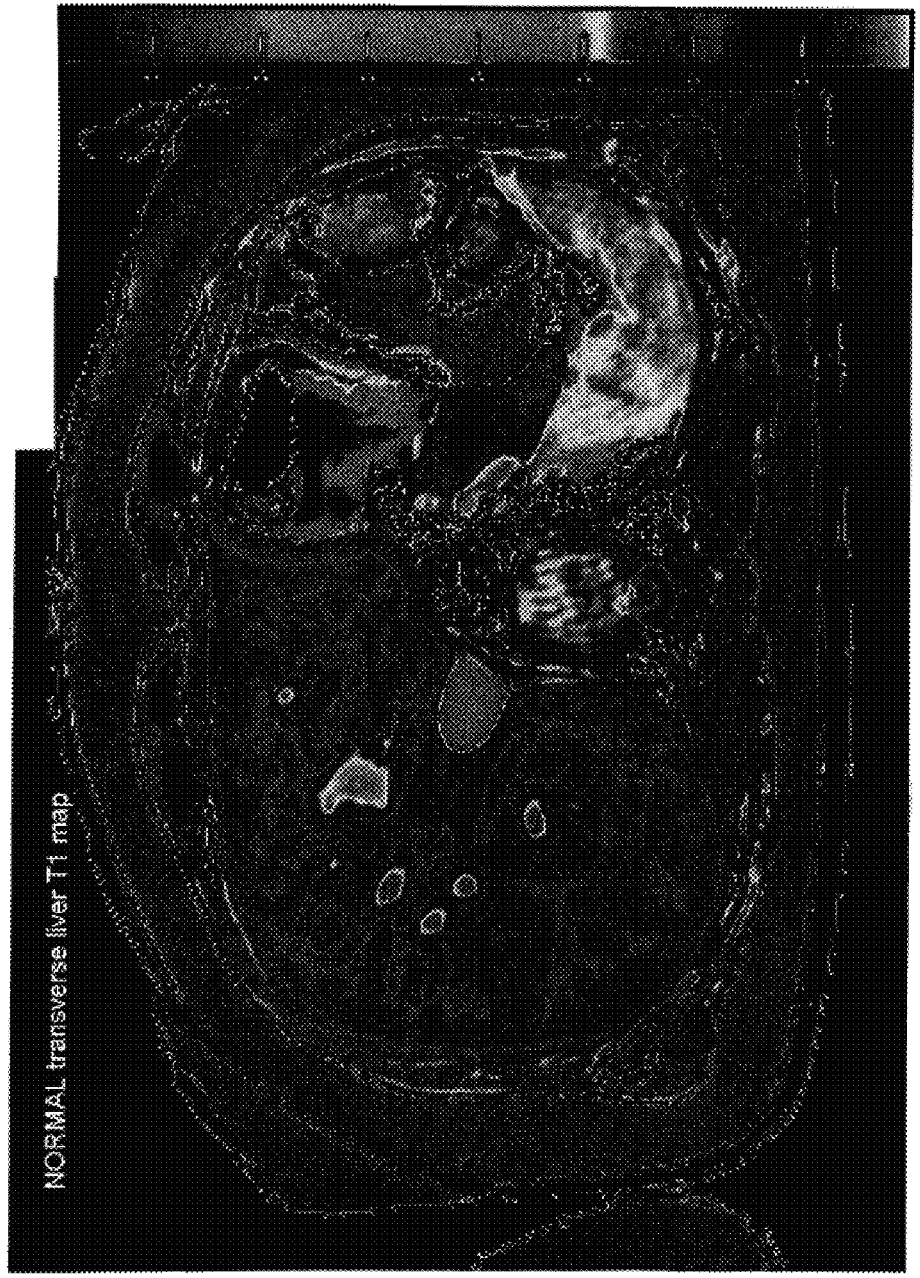
FIGS. 2A and B are representative transverse plane T1 maps of liver obtained using Sh-MOLLI at 3 Tesla, FIG. 2A depicting a normal transverse liver T1 map and FIG. 2B depicting a transverse liver T1 map of a patient with liver fibrosis and a high T1 value (1050 ms).
Figure 2B:
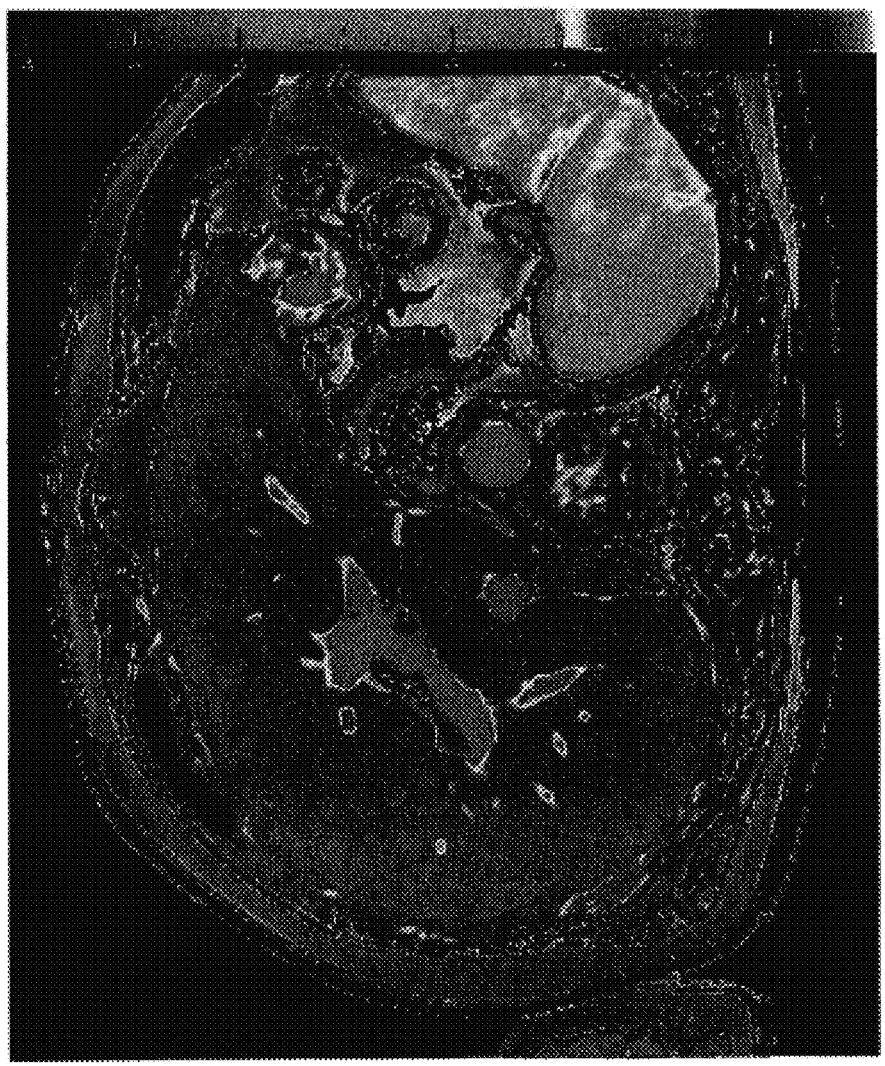

Specifically, in patients presenting hepatic disease, preliminary data shows that the Sh-MOLLI technique is able to distinguish fibrosis from normal liver, with areas of long T1 correlating with evidence of increased tissue fibrosis in biopsy samples. For example, FIGS. 2A and 2B are representative transverse plane T1 maps of liver using the Sh-MOLLI technique at 3 Tesla. FIG. 2A depicts a normal transverse liver T1 map. FIG. 2B, however, depicts a transverse liver map of a patient with liver fibrosis and high T1 value (1050 ms).

In a study involving 50 healthy volunteers, each presumed to have a normal liver, and twelve patients with suspected liver disease, the ranges for T1 for the 50 normal volunteers (i.e., the "normal ranges") were determined as 786±110 ms. Hepatic lipid content (HLC) was measured in 100 normal volunteers, determined as having a body mass index (BMI) in the range of 18-30 kg/m². Normal HLC was determined as 1.3±3.4%, with a median of 0.75% and an interquartile range of 0.47-1.25% (0-4.7%).

HLC measured by MR spectroscopy (MRS) correlated well with histological assessment (liver biopsy) for hepatic steatosis, with $r_s$=0.80 and p=0.005.

Figure 3:
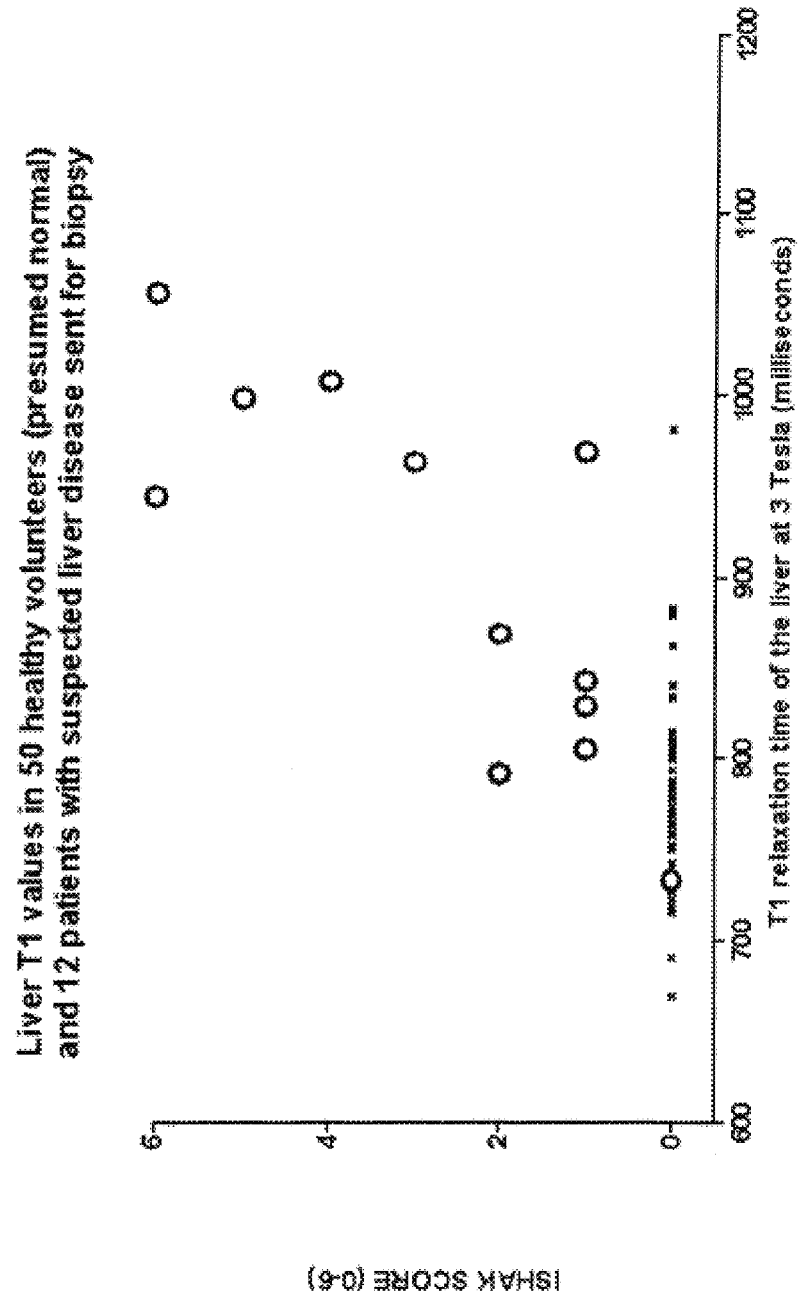
FIG. 3 is a graph showing that T1 varies with fibrosis in liver patients and 50 healthy volunteers.

For the 12 patients suspected as having liver disease, liver fibrosis was detectable with T1 mapping. Not only was there a clear correlation between T1 and ISHAK score ($r_s$=0.89 and p<0.001, FIG. 3), but every patient with significant fibrosis had T1>900 ms, and all normal patients with T1<900 ms had minimal or no fibrosis (<1/6 on ISHAK). Thus, in this sampling a T1 threshold of 900 ms correctly identified all fibrosis patients, with one "false" positive. In these patients without significant fibrosis (5/10), exclusion of significant disease would have meant they did not need liver biopsy, thus reducing patient risk.

Figure 4:
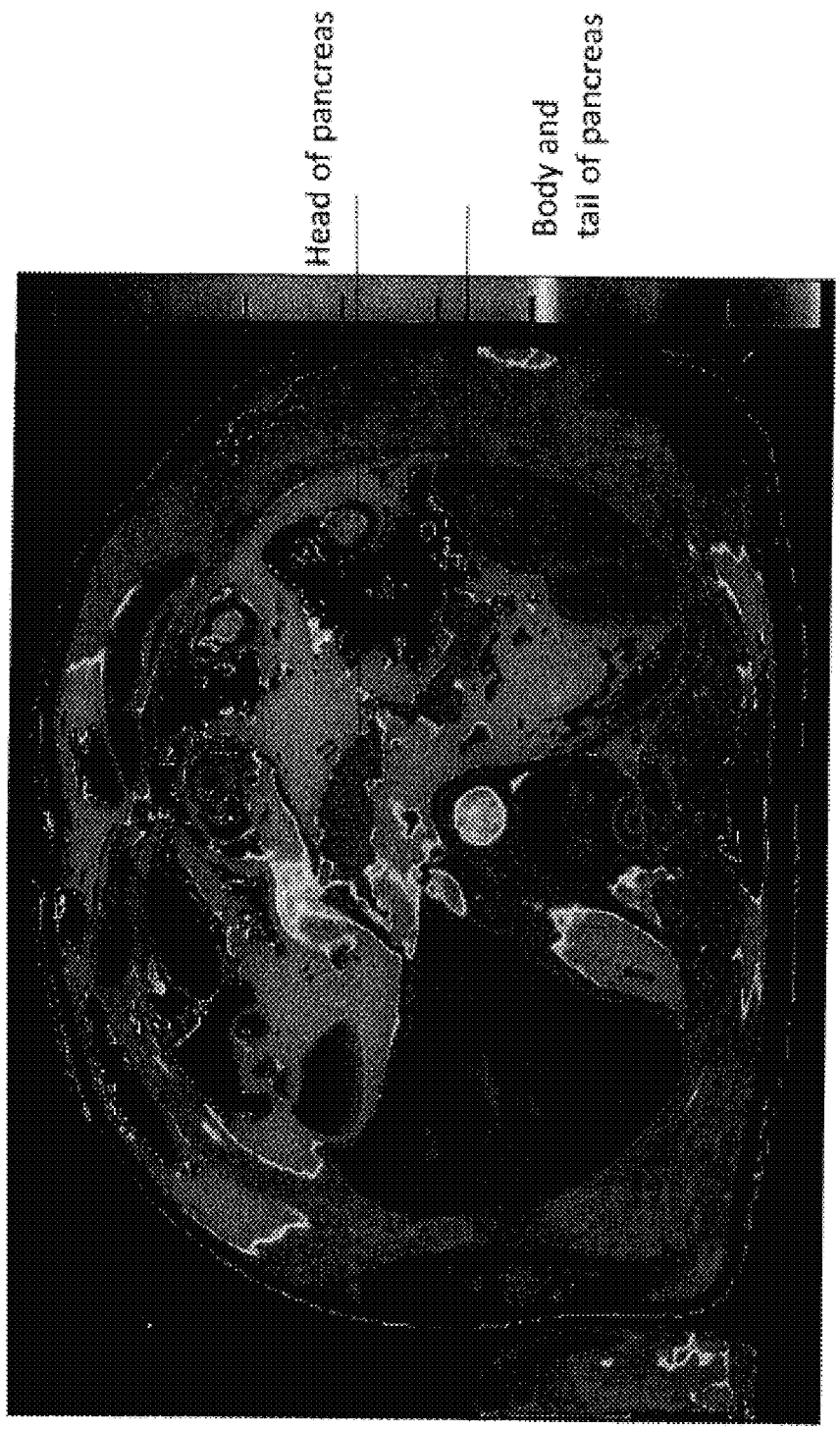
FIG. 4 is a representative T1 map of a pancreas obtained using Sh-MOLLI at 3 Tesla.

Due to demonstrated good measurement properties over wide range of T1 values the Sh-MOLLI technique can be a superior method for in vivo contrast and non-contrast quantitative T1-mapping of liver and pancreas (FIG. 4) or any other tissue where interference from pulsatile vascular motion is of concern, particularly in patients with potential respiratory comorbidity that may allow only short breath-holds and in whom invasive biopsies would carry high risk. FIG. 4 depicts a T1 map accurately showing the outline and structure of a pancreas. This data shows that T1 mapping alone can serve as a marker for hepatic and/or pancreatic disease, particularly when using the Sh-MOLLI technique.

One embodiment of the Sh-MOLLI technique is a method for performing T1 mapping requiring only a relatively short breath-hold. The method comprises performing consecutive inversion-recovery (IR) experiments that include front-loaded sampling followed by one or more subsequent experiments yielding a set of additional samples. The method further comprises conditionally including the subsequent one or more samples for the T1-mapping based on several concurrent estimates of T1 recovery time and respective fit errors associated with the subsequent samples.

In a further embodiment, T1 values that are larger than a predetermined interval (e.g., the heartbeat interval) are considered adequately estimated using just a single inversion recovery (IR) experiment. Additional IR experiments are used typically only to estimate short T1 values based on the respective estimates and the measures of additional improvement in the recovery curve. Thus, in an embodiment of the Sh-MOLLI technique, minimal recovery times are combined with conditional data reconstruction. In one embodiment, the conditional data reconstruction is conducted algorithmically based on certain conditions, equivalent to using binary weighting of input parameters. In another embodiment, the conditional data processing is achieved using weighted processing, for example using weights from a continuous scale.

Multiple datasets including a front-loaded data set are utilized based on original data to determine the inclusion of potentially suboptimal data samples. In accordance with such embodiments, progressive fitting of linear or non-linear models for these data sets are used to identify and reject samples identified as being suboptimal from available measurements. As described below, a first embodiment is directed to binary weighting of input parameters in model identification. While some embodiments incorporate binary weighting of input parameters in model identification, alternative embodiments incorporate weighting on a continuous scale whereby all samples are used.

In one embodiment of a Sh-MOLLI sequence, a first front-loaded group of samples with presumed optimal parameters is collected and fitted. Based on the results obtained from the first group of samples, additional samples and non-linear fitting may or may not be performed to improve accuracy over an extended range of parameters. Conditional data processing is performed and additional solutions are accepted when solutions fall within predetermined limits. Specifically, for some embodiments, additional solutions are accepted if the new solution is characterized by improved fit quality. Furthermore, a limit is placed on the processing time where further solutions are not sought when previous steps indicate that they are not necessary.

Figure 5A:
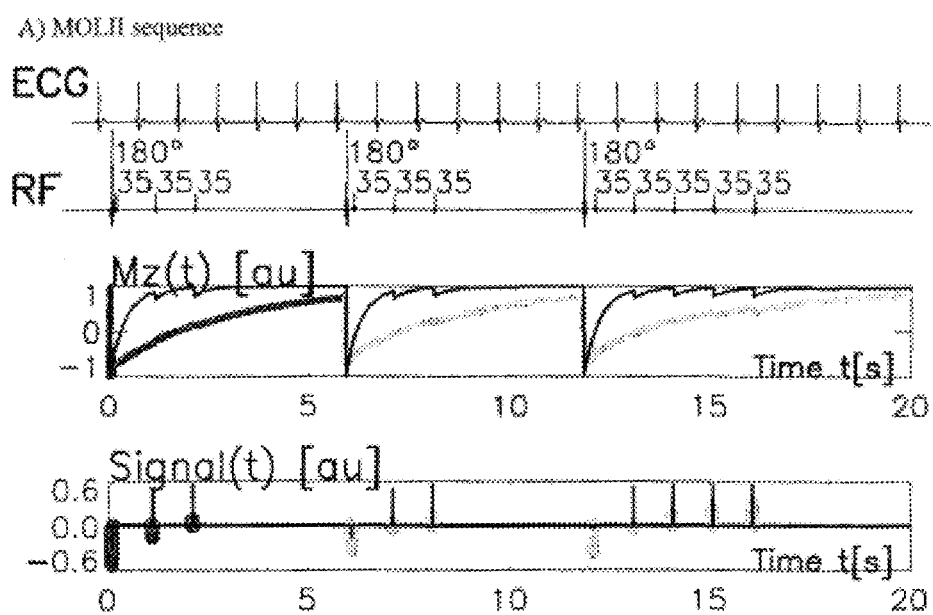
FIGS. 5A-B show a side-by-side simulated comparison of ECG-gated pulse sequence schemes for simulation of a) MOLLI and b) Sh-MOLLI at a heart rate of 60 bpm for T1 mapping of the liver.
Figure 5B:
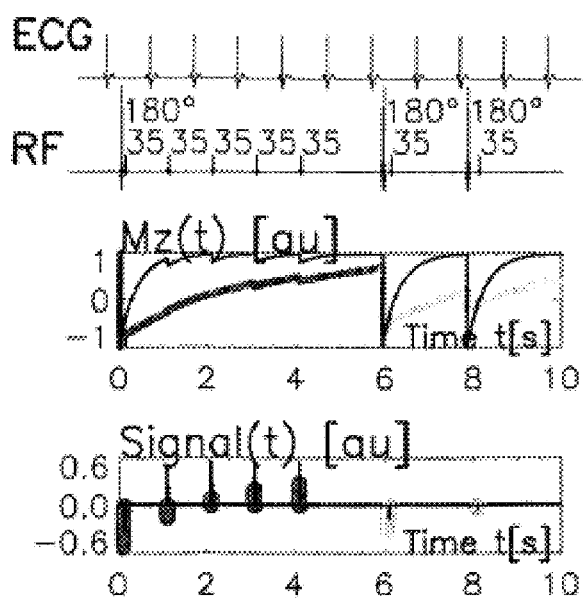

Reference is made to FIGS. 5A and 5B, which show a side-by-side simulated comparison of ECG-gated pulse sequence schemes for simulation of a) MOLLI and b) Sh-MOLLI at a heart rate of 60 bpm. Steady-state free precession (SSFP) readouts are simplified to a single 35° pulse each, presented at a constant delay time TD from each preceding R wave. The 180° inversion pulses are shifted depending on the IR number to achieve the desired shortest T1 (which may be but are not limited to such values as 100, 180 and 260 ms) in the consecutive inversion recovery (IR) experiments.

The plots shown in FIGS. 5A-B represent the evolution of longitudinal magnetization (Mz) for short T1 (400 ms, thin traces) and long T1 (2000 ms, thick lines). Note that long epochs free of signal acquisitions minimize the impact of incomplete Mz recoveries in MOLLI so that all acquired samples can be pooled together for T1 reconstruction. For Sh-MOLLI, the validity of additional signal samples from the 2nd and 3rd IR epochs is determined on-the-fly by progressive non-linear estimation so they can be used when deemed necessary or rejected when invalid.

Simulations were performed in IDL (Interactive Data Language ver. 6.1, ITT Visual Information Solutions) by implementing equations for the piece-wise calculation of longitudinal magnetization (Mz(t)) and the signal samples generated by a train of arbitrarily-spaced ideal excitation pulses. Inversion pulses were assumed to be perfect 180° excitations, and readout pulses were 35°. Both sequences had three IR epochs. Simulations were performed for MOLLI based on its optimized variant, which collects 3+3+5 samples in three consecutive IR epochs separated by long recovery periods (FIG. 5A).

As shown in FIG. 5B, with the Sh-MOLLI technique, 5+1+1 samples were collected in less than 10 heartbeats. It should be emphasized that the 5+1+1 sequence here is just one of various possible sequences that may utilized for Sh-MOLLI, and other sequence schemes may be implemented. IR epochs were separated by only one TRR (R-R interval). Abbreviated Sh-MOLLI recovery epochs mean that Mz can be severely affected by preceding IR epochs in the Sh-MOLLI sequence (FIG. 5B) so that the signal samples from the 2nd and 3rd IR obtained using Sh-MOLLI do not fit the IR equations as outlined for MOLLI. This problem is circumvented by conditional data analysis according to the algorithm described in more detail below.

For this example, given an adequate signal level, non-linear identification of T1 is always performed for samples 1-5 (S1-5) from the 1st IR, with samples from the 2nd (S6) and 3rd (S7) IR being used only if the estimated T1 values are short (<TRR) or very short (<0.4 TRR), respectively. Thus, in this embodiment, use of sample datasets S1-6) are accepted only if estimated T1 falls below a heartbeat interval (TRR), and use of sample datasets S1-7 are accepted only if estimated T1 falls below 0.4 TRR. The final T1 is accepted only if the quality of fit sufficiently improves in comparison to the TRR. Simulations using both sequences outlined in FIGS. 5A-B were performed for T1 ranging from 50 to 2700 ms (50 ms increments) and for heart rate (HR) between 40-100 bpm (20 bpm increments) and adding noise representative of measurement conditions.

Having described the basic framework, details for implementing Sh-MOLLI are now described, which combines minimal recovery times with conditional data reconstruction. Embodiments of Sh-MOLLI may be implemented as 2, 3, or more inversion-recovery (IR) experiments split over a predetermined number of heartbeats to collect SSFP images with varying T1, typically on the order of 100-5000 ms, whereby the first IR experiment is "front-loaded" with more pulses. Conditional data processing is then performed to determine whether subsequent samples are to be included and with what impact they have on the final estimate.

Figure 6:
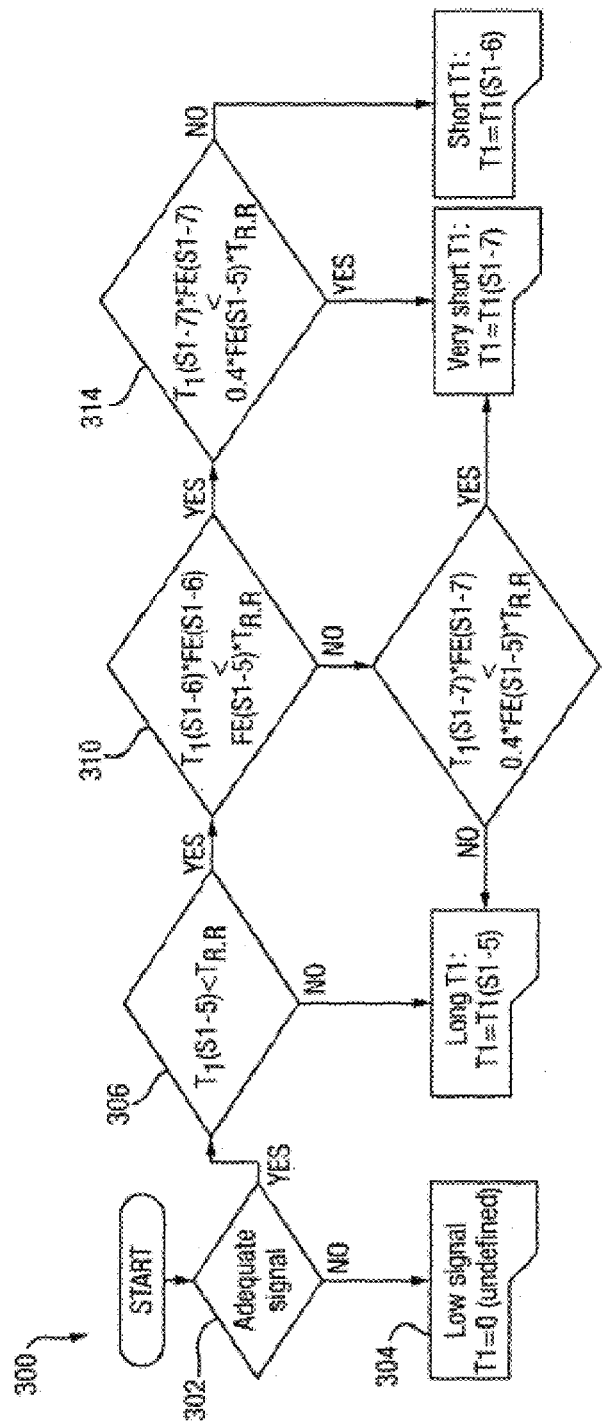
FIG. 6 is a flow chart for performing conditional data processing to establish appropriate processing sequence for example "long," "short," and "very short" T1 categories for T1 mapping of the liver.

Reference is made to FIG. 6, which is a flow chart 300 for performing one embodiment of the Sh-MOLLI conditional data processing. An algorithm is implemented for the inclusion of samples to circumvent the impact of sub-optimally short recovery epochs in T1 estimation. The fit error (FE) is calculated as the square root of the sum of squared residuals divided by number of samples minus one. "S1-5" denotes the set of samples from the first inversion recovery. "S1-6" and "S1-7" denote the set of samples from the first inversion recovery supplemented by samples from consecutive IR experiments. $T_{R-R}$ is a heartbeat interval.

Note that while the first data set comprises 5 pulses followed by 1+1 pulses for this non-limiting example, the data sets are not limited to these numbers and other front-loaded schemes (e.g., 5+2+1, 5+1+2) may be implemented. In some embodiments, a front-loaded scheme can be implemented in which the number of samples from the first experiment exceeds the number of samples from a subsequent experiment. In other embodiments, a front-loaded scheme can be implemented in which the number of samples from the first experiment exceeds the number of samples from all subsequent experiments. Samples are obtained with potentially sub-optimally short recovery periods due to repeated Look-Locker Inversion recovery experiments (Piechnik S K, Ferreira V M, Dall'Armellina E, Cochlin L E, Greiser A, Neubauer S, Robson M D., Shortened Modified Look-Locker Inversion recovery (ShMOLLI) for clinical myocardial T1-mapping at 1.5 and 3 T within a 9 heartbeat breathhold, J Cardiovasc Magn Reson. 2010 Nov. 19; 12:69) contained within a single breath-hold. The fit error (FE) described above may also be replaced by another numerical representation of the empirical data consistency.

In accordance with one embodiment, conditional data processing is performed and Sh-MOLLI samples from the second and third IR are taken into account only if: 1) the estimated T1 is shorter than the R-R interval; and 2) if the second and third IR experiments improve non-linear fit. In the non-limiting example shown, a specific sampling method involving 5+1+1 samples in three IR experiments is used, separated by single recovery epochs.

In decision block 302, if an adequate signal is not present, then a low signal exists and processing stops (block 304). A predefined threshold may be used for this determination. An initial fit is performed using the first 5 samples, resulting in a T1 (S1-5) estimate—the recovery time for the first 5 samples. Processing continues based on whether the estimated T1 time is long (meaning equal to or longer than a heartbeat interval $T_{R-R}$) or short (meaning less than a heartbeat interval) (decision blocks 306, 310, 314).

For some embodiments, subsequent fits are performed to improve accuracy for the short T1 samples, only if T1 (S1-5) is less than the RR-period, the time between heartbeats (decision block 306). That is, if the T1 time for the first 5 samples is relatively short, subsequent samples are considered. Finally, the sample datasets of S1-6 and S1-7 are accepted and performed only if the estimated T1 falls below $T_{R-R}$ and $0.4*T_{R-R}$ respectively. Furthermore, the fit error (FE) normalized by the number of samples must be lower than the FE based on the first 5 samples (decision blocks 310, 314). Thus, a determination is made on how well subsequent samples (samples 6 and 7 in the non-limiting example of FIG. 6) match the recovery curve. This is done to ensure that noise and interference is not introduced by the latter samples following the front-loaded samples. Conditional reconstruction of incomplete recovery periods ensures that T1-mapping with a level of accuracy comparable to that by the MOLLI technique can be achieved in a shorter heartbeat breath-hold.

Figure 7:
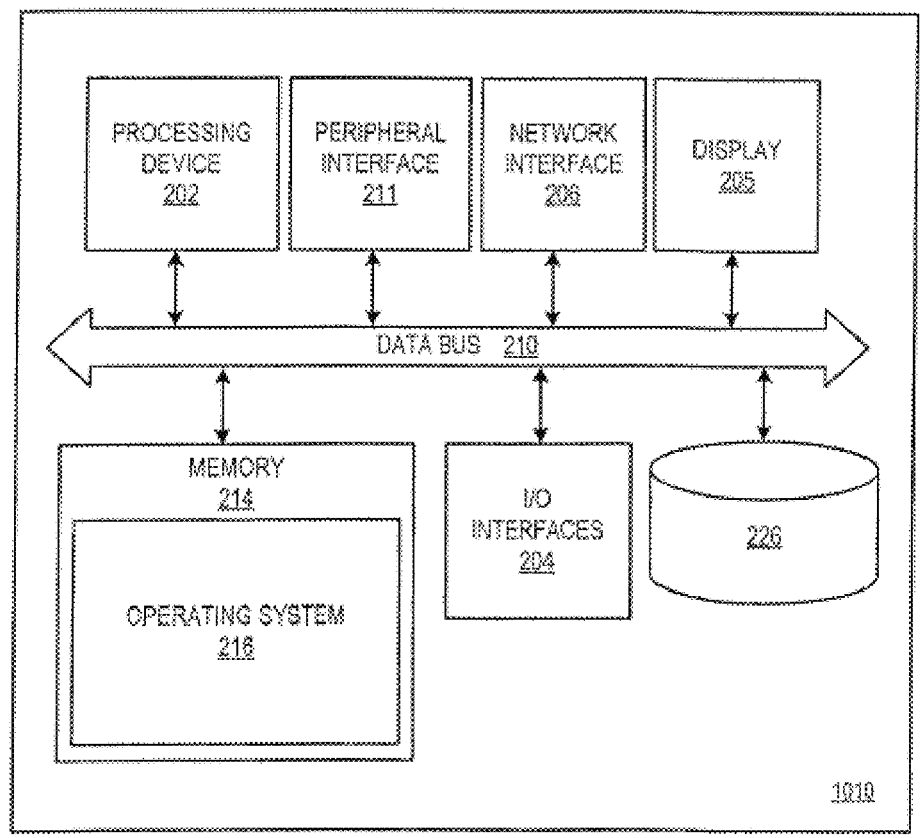
FIG. 7 is a schematic block diagram of an apparatus in which embodiments of the universal systems and methods for mapping of visceral organs disclosed herein may be implemented.

Reference is now made to FIG. 7, which depicts an apparatus 1010 in which the systems and methods for performing multi-parametric magnetic resonance diagnosis of a liver described herein may be implemented. The apparatus 1010 may be embodied in any one of a wide variety of wired and/or wireless computing devices, multiprocessor computing device, and so forth. As shown in FIG. 7, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for performing multi-parametric magnetic resonance diagnosis of liver disease described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 7, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over a network 118. The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 7 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate immediate T1 maps available for viewing immediately after image acquisition, thereby allowing re-acquisition on-the-spot if necessary. Examples of apparatus in which the MOLLI and Sh-MOLLI sequences may be implemented are described in U.S. Pat. No. 5,993,398 and U.S. Pat. No. 6,245,027 and U.S. Patent Application Publication No. 2011/0181285, which are incorporated by reference as if fully set forth herein.

The flowcharts of FIGS. 1 and 6 show examples of functionality that may be implemented in the apparatus 1010 of FIG. 7. If embodied in software, each block shown in FIGS. 1 and 6 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 7) in a computer system or other system. The machine code may be converted from the source code, etc. If embodied in hardware, each block may represent a circuit or a number of interconnected circuits to implement the specified logical function(s).

Although the flowcharts of FIGS. 1 and 6 show a specific order of execution, it is understood that the order of execution may differ from that which is depicted. For example, the order of execution of two or more blocks may be scrambled relative to the order shown. Also, two or more blocks shown in succession in FIGS. 1 and 6 may be executed concurrently or with partial concurrence. Further, in some embodiments, one or more of the blocks shown in FIGS. 1 and 6 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A computer-implemented method for performing spin-lattice (T1) mapping of visceral organs, comprising:
  a) positioning a subject in association with a magnetic resonance (MR) scanner for performing the T1 mapping;
  b) selecting a region of the subject having one or more visceral organs of interest for the T1 mapping;
  c) detecting, by a computing device, whether heart associated motion is present in the selected region;
  d) artificially triggering the T1 mapping of the selected region, by the computing device, if no heart associated motion is detected;

e) determining, by the computing device, whether either high heart rate or irregular heart beat is present, when heart associated motion is detected;

f) triggering the T1 mapping of the selected region by heart beat, by the computing device, when neither high heart rate nor irregular heart beat are detected;

g) artificially triggering the T1 mapping of the selected region, by the computing device, when either high heart rate or irregular heart beat are detected; and h) upon triggering the T1 mapping in either step d), f), or g), acquiring T1 maps of the one or more visceral organs of interest in the selected region using the magnetic resonance (MR) scanner.

2. The method of claim 1, wherein when T1 mapping is artificially triggered it is artificially triggered using simulated ECG.

3. The method of claim 1, wherein one or more of shimming, frequency shifting, and fat saturation are performed, as needed, for image quality assessment of the acquired T1 maps.

4. The method of claim 1, wherein the T1 mapping is performed using repeated inversion recovery experiments.

5. The method of claim 1, wherein the T1 mapping is performed using consecutive inversion-recovery (IR) experiments that include front-loaded sampling followed by one or more subsequent samples; and
conditionally including the one or more samples for the T1 mapping based on empirical relationships between estimated spin-lattice relaxation time T1, heart rate, heart beat period or experimentally achieved relaxation recovery times or degrees, and estimated fit error associated with subsequent experiments and samples.

6. The method of claim 5, wherein a number of samples from a first consecutive inversion-recovery (IR) experiment exceeds the number of samples from a subsequent experiment.

7. The method of claim 1, wherein the T1 mapping is performed using consecutive inversion-recovery (IR) experiments, wherein the consecutive inversion-recovery (IR) experiments comprise a first IR experiment, a second IR experiment, and a third IR experiment, the first IR experiment comprising a number of samples exceeding a number of samples of both the second IR experiment and the third IR experiment; and
conditionally processing the samples in the first, second, and third IR experiments.

8. The method of claim 7, wherein conditionally processing the samples in the first IR experiment comprises:
determining an initial spin-lattice (T1) estimation; and
based on the initial T1 estimation, determining whether a T1 value associated with the samples in the first IR experiment is less than a heartbeat interval.

9. The method of claim 7, wherein the first, second, and third IR experiments split over a predetermined number of heartbeats, wherein the first IR experiment is front-loaded with respect to the second and third IR experiments.

10. A system, comprising:
a magnetic resonance (MR) scanner;
at least one computing device having a processor and a memory; and
at least one application executable in the at least one computing device stored in the memory that, when executed by the processor, the application causes the at least one computing device to at least:
a) select a region of a subject having one or more visceral organs of interest for T1 mapping;

b) detect whether heart associated motion is present in selected region, wherein the presence of heart associated motion is determined by the presence of a heart associated motion artifact in an image obtained using the MR scanner;

c) artificially trigger the T1 mapping of the selected region if no heart associated motion is detected;

d) determine whether either high heart rate or irregular heart beat is present when no heart associated motion is detected;

e) trigger the T1 mapping of the selected region by heart beat when neither high heart rate nor irregular heart beat are detected;

f) artificially trigger the T1 mapping of the selected region when either high heart rate or irregular heart beat are detected; and g) acquire, upon triggering the T1 mapping of step c), e), or f), T1 maps of the one or more visceral organs of interest in the selected region using the magnetic resonance (MR) scanner.

11. The system of claim 10, wherein when T1 mapping is artificially triggered it is artificially triggered using simulated ECG.

12. The system of claim 10, wherein one or more of shimming, frequency shifting and fat saturation are performed, as needed, for image quality assessment of the acquired T1 maps.

13. The system of claim 10, wherein the T1 mapping is performed using repeated inversion recovery experiments.

14. The system of claim 10, wherein, when executed, the application further causes the at least one computing device to perform consecutive myocardial inversion-recovery (IR) experiments comprising a first, second, and third IR experiment, wherein the consecutive myocardial inversion-recovery (IR) experiments have a corresponding number of samples, and wherein the first IR experiment is front-loaded relative to the second and third IR experiments; and
logic that conditionally utilizes spin-lattice (T1) samples in the first, second, and third IR experiments for non-linear T1 fitting based on T1 relaxation times.

15. The system of claim 14, wherein the number of samples from the first experiment exceeds the number of samples from a subsequent experiment.

16. A system, comprising:
a magnetic resonance (MR) scanner;
at least one computing device having a processor and a memory; and
at least one application executable in the at least one computing device stored in the memory that, when executed by the processor, causes the computing device to at least:
a) select a region of a subject having one or more visceral organs of interest for T1 mapping;

b) detect whether heart associated motion is present in selected region;

c) if no motion is detected, artificially trigger T1 mapping of the selected region;

d) if heart associated motion is detected, also determine whether either high heart rate or irregular heart beat is present;

e) if neither high heart rate, nor irregular heart beat is present, then trigger T1 mapping of the selected region by heart beat;

f) if either high heart rate or irregular heart beat are present, then artificially trigger T1 mapping of the selected region; and g) acquire T1 maps of the one or more visceral organs of interest in the selected region based on the triggering of the T1 mapping using the magnetic resonance (MR) scanner.

\* \* \* \* \*